United States Patent [19]

Bauers et al.

[11] 4,199,987
[45] Apr. 29, 1980

[54] ELECTRONIC SYSTEM FOR MEASURING TIME, IMPACT ENERGY AND OTHER ATHLETIC PARAMETERS

[75] Inventors: William R. Bauers, 2802 N. Bristol St., Apt. No. 43, Santa Ana, Calif. 92706; Paul Mioduski; Claude R. Ceccon, both of Tucson, Ariz.

[73] Assignee: William Roy Bauers, Santa Ana, Calif.

[21] Appl. No.: 965,103

[22] Filed: Nov. 30, 1978

[51] Int. Cl.² .............................................. B01L 5/02
[52] U.S. Cl. ..................................................... 73/379
[58] Field of Search .................. 73/379, 12, 11, , 492; 272/76; 128/2 N, 2 S

[56] References Cited

U.S. PATENT DOCUMENTS

| | | | |
|---|---|---|---|
| 1,199,278 | 9/1916 | Koch | 272/76 |
| 3,712,122 | 1/1973 | Harris | 73/492 |
| 4,027,875 | 6/1977 | Hurley | 272/76 |
| 4,055,842 | 10/1977 | Yakshin | 73/12 |

Primary Examiner—S. Clement Swisher
Assistant Examiner—Denis E. Corr
Attorney, Agent, or Firm—Jackson, Jones & Price

[57] ABSTRACT

An electronic system for selectively measuring predetermined athletic parameters, such as reaction time and impact energy, and for displaying the results of the measurements is disclosed. The system includes transducer apparatus for sensing a participant's athletic reaction or motion, a selectively actuable timing circuitry responsive to initiation for providing after a pseudo-random delay a start signal to which the participant is to respond, and logic circuitry responsive to the transducer output. The timing circuit utilizes information provided by the logic circuitry and provides outputs indicative of predetermined parameters of the participant's motion or reaction time. The disclosed system further includes display apparatus responsive to the timing circuit outputs for displaying indicia of the measured parameters.

11 Claims, 4 Drawing Figures

ELECTRONIC SYSTEM FOR MEASURING TIME, IMPACT ENERGY AND OTHER ATHLETIC PARAMETERS

BACKGROUND OF THE INVENTION

The disclosed invention relates to training and testing apparatus, and particularly to apparatus for measuring parameters of a participant's athletic reaction and/or motion. The disclosed invention is particularly advantageous for measuring reaction time in response to a start signal and the impart energy of participant initiated motion.

The prior art includes various athletic devices which give an indication of reaction time or the force delivered to a punching or striking bag. For example, U.S. Pat. No. 4,027,875, issued to Hurley on June 7, 1977, discloses a reaction timing device wherein a digital counter is started by a first switch and stopped by a separate second switch, thereby indicating elapsed time. In use, both switches are contemplated to be actuated by one participant or by two participants.

U.S. Pat. No. 1,199,278, issued to Koch on Sept. 26, 1916, discloses a punching apparatus which utilizes mechanical displacement against a known pressure to indicate the force of the blow delivered to a punching bag.

U.S. Pat. No. 4,055,842, issued to Takshin et al on Oct. 25, 1977, discloses a digital impact pulse measuring system which measures single and multiple impact pulses and includes a readout device for showing the measured values. Specifically, the system disclosed in Tashkin et al measures the peak value of impact pulses.

However, prior art measuring systems, such as those discussed above, suffer from several disadvantages. For example, prior art devices generally use mechanical apparatus for sensing and measuring force and motion. Also, prior art devices are generally designed for a particular application and are not readily adapted for a variety of applications. Further, prior art reaction time measuring devices utilize a start signal which is controlled by the participant or is readily anticipated. A further problem with prior art devices is that they measure instantaneous values of force and do not indicate the amount of the energy delivered by a participant.

It is therefore an object of the disclosed invention to provide an improved reaction time measuring system.

It is a further object of the invention to provide an improved impact energy measuring system.

Still another object of the invention is to provide a reaction time measuring system wherein the start signal to the participant cannot be anticipated by the participant, thereby resulting in a realistic measurement of reaction time.

Yet another object of the invention is to provide an athletic impact energy measuring system which measures the total energy transmitted by a participant.

SUMMARY OF THE INVENTION

The disclosed invention advantageously achieves the foregoing objects and features by providing a measuring system having transducer apparatus responsive to a predetermined motion by a participant and circuitry which utilizes the transducer output to provide signals indicative of reaction time and impact energy. Specifically, the system further includes a triming circuit which provides a start indicating signal after a pseudo-random time delay initiated by the participant, and logic circuitry responsive to the transducer apparatus. The timing circuit utilizes the output of the logic circuitry and provides an output indicative of the elapsed time between the occurrence of the start signal and the occurrence of a predetermined motion sensed by the transducers. The timing circuit also functions to provide another output which is indicative of the amount of energy transmitted by the participant's motion in response to the transducer outputs.

BRIEF DESCRIPTION OF THE DRAWING

The foregoing and other objects, features and advantages of the disclosed invention can be readily understood by one skilled in the art from the detailed description of the disclosed system and the drawing wherein.

DETAILED DESCRIPTION OF THE DISCLOSURE

Figure 1:
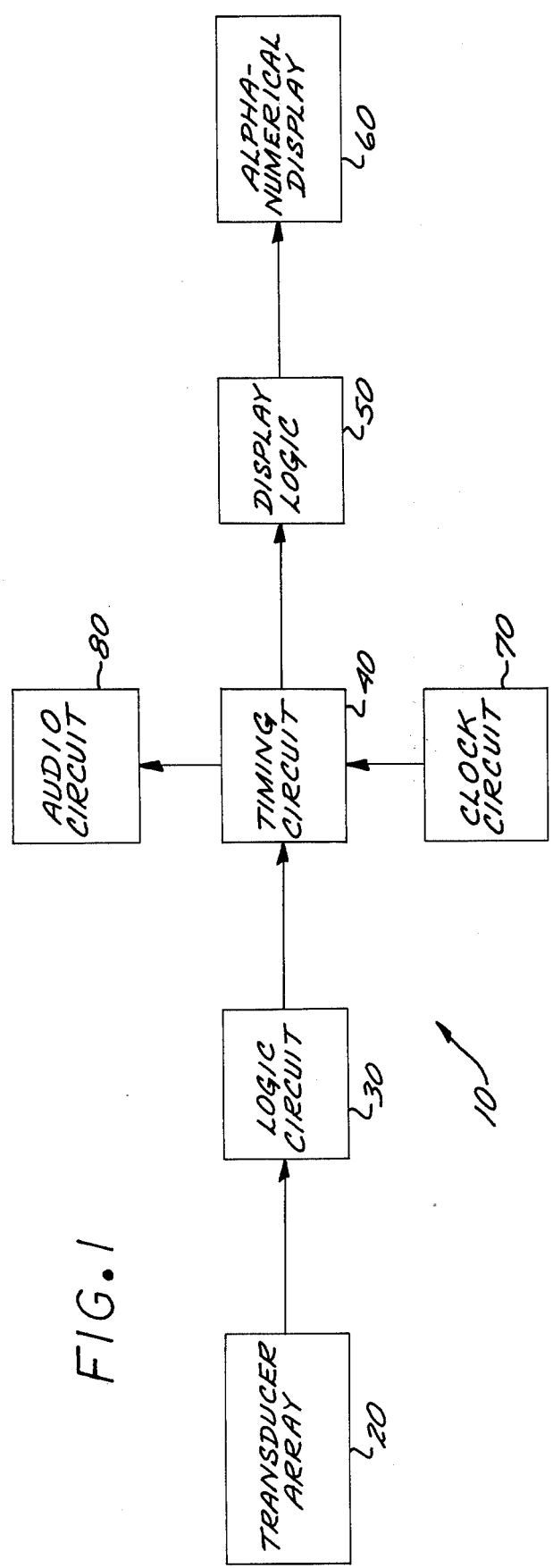
FIG. 1 is a block diagram of the overall aspects of the disclosed system.

FIG. 1 is a block diagram representation of the disclosed athletic parameter measuring system 10, and includes, generally, a transducer 20, a logic circuit 30, a timing circuit 40, display logic 50, and an alpha-numeric display 60. The system 10 further includes a clock circuit 70. Specific preferred embodiments of the elements of the system 10 will be described in more detail below. However, the broad functions of the elements of the system 10 will first be described in order to facilitate an understanding of the overall system concepts.

The transducer 20 is appropriately attached to or incorporated in some form of athletic apparatus and senses the impact or motion transmitted to the athletic apparatus by the participant. The logic circuit 30 is responsive to the outputs of the transducer array and provides an output during the time the impact or motion transmitted by the participant exceeds a predetermined threshold level.

The timing circuit 40 provides several functions in the course of the measuring procedure. It is responsive to the actuation of a switch by the participant, or some other person, and provides an initial fixed delay followed by a pseuod-random delay. After such total delay, the timing circuit provides a start signal which is utilized by the audio circuit 80 to audibly indicate to the participant the start of the reaction time measurement period. The same start signal is utilized to cause clocking pulses to be transmitted to the display logic 50. The start signal remains present until the logic circuit 30 provides an output indicating that impact has started, at which time the clocking pulses to the display logic 50 are terminated. The count of the clocking pulses to the display logic for the duration of the start signal can then be utilized to provide the reaction time on the alphanumeric display 60 as controlled by the display logic 50.

The timing circuit 40 is further responsive to the duration of the output of the logic circuit 30. For the duration of an output indicating an impact, the timing circuit 30 provides to the display logic clocking pulses which are utilized to appropriately display an indication of impact energy. Of course, as can be appreciated by one skilled in the art, the display logic would be adapted to cause the display of the measured parameters in appropriate units of measure, and in a predetermined or selected manner. Also, the display logic could be readily adapted to appropriately cause the display of the energy of each of a series of impacts sensed by the logic circuit 30.

The clock circuit 70 provides the timing circuit 40 with the appropriate clock pulses for utilization with respect to controlling the application of clocking pulses to the display logic 50.

Figure 2:
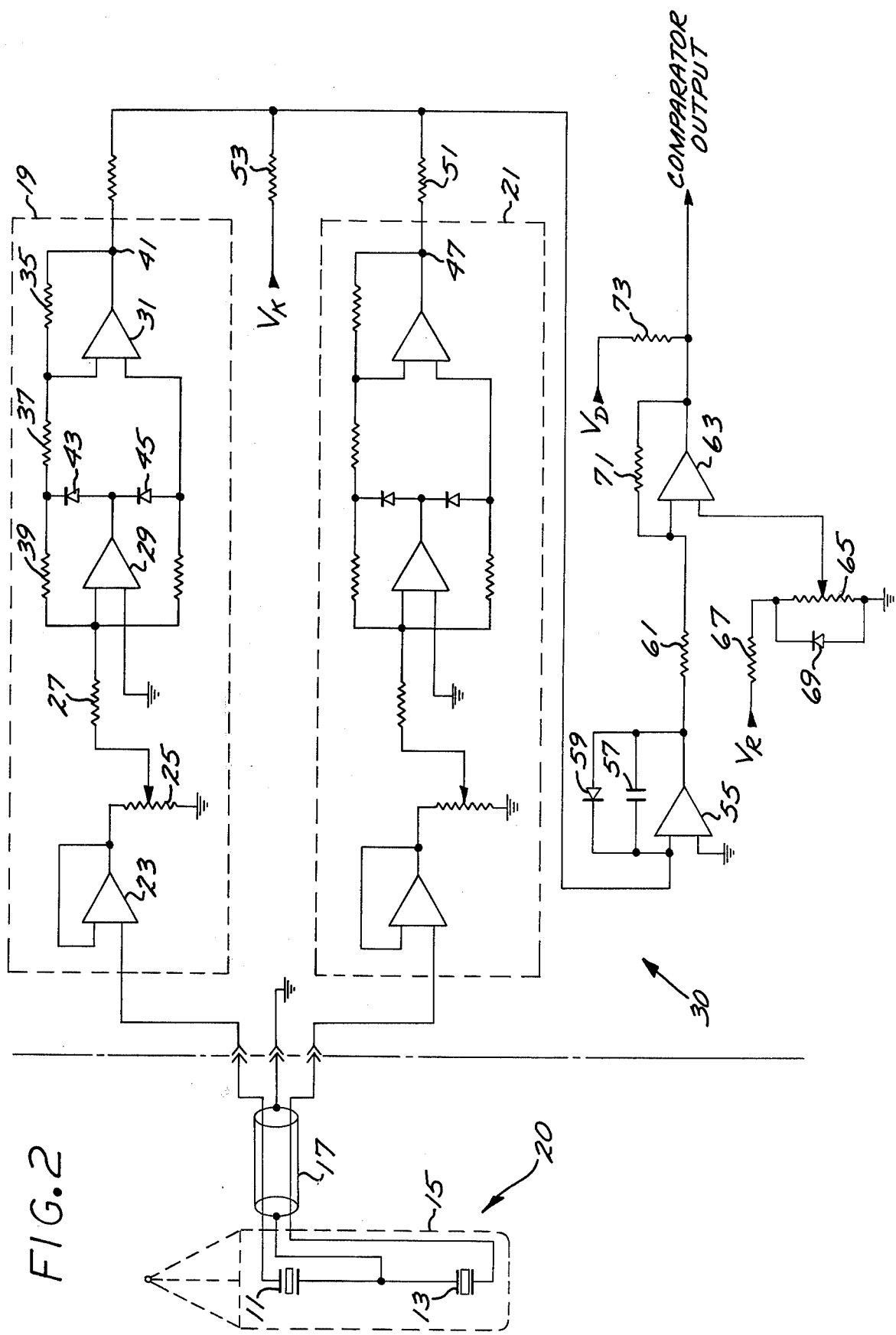
FIG. 2 is a circuit diagram of the logic circuitry of the disclosed system which provides an indication of the occurrence and duration of a predetermined impact or motion by a participant.

With reference to FIG. 2, the transducer array is shown as including crystal microphones 11 and 13 appropriately disposed in a punching bag 15. The microphones 11 and 13 are preferably equidistant from the center of a designated striking area on the punching bag 15, and should face toward one another. The outputs of the microphones are coupled via a shielded cable 17 to respective buffering rectifiers generally designated as 19 and 21. Since the elements of each buffering rectifier 19, 21 are identical, only the elements of the buffering rectifier 19 will be described.

The microphone input for the buffering rectifier 19 is applied to the non-inverting input of an operational amplifier 23 which is configured in a voltage follower configuration. The output of the operational amplifier 23 is coupled to one end of a variable resistor 25, which has its other end coupled to ground. The use of variable resistors in each buffering rectifier 19 and 21 allows for the normalization of each of the microphones 11 and 13. The tap terminal output of the variable resistor 25 is provided through a coupling resistor 27 to a precision rectifier which includes operational amplifiers 29 and 31. The operational amplifier 31 is provided with the buffered microphone output through a coupling resistor 33. Feedback resistors 35, 37 and 39 are coupled between the output terminal 41 of the operational amplifier 31 and the inverting inputs of the operational amplifiers 29 and 31. Diodes 43 and 45 are coupled between the output of the operational amplifier 29 and the junction between the feedback resistors 37 and 39, and between the output of the operational amplifier 29 and the non-inverting input of the operational amplifier 31, respectively. Therefore, the signal at the output terminal 41 of the buffering rectifier 19 is indicative of the absolute value of the impact pulse as seen by the corresponding microphone 11. Similarly, the output at the terminal 47 of the buffering rectifier 21 is indicative of the absolute value of the impact pulse as seen by the corresponding microphone 13.

The outputs of the buffering rectifiers 19 and 21, are summed together through resistors 49 and 51, respectively, along with a source of constant voltage $V_k$ which is applied through a resistor 53. The sum thus formed is applied to the inverting input of an operational amplifier 55 which is configured as an integrator. A feedback capacitor 57 and a clamping diode 59 are coupled in parallel between the output of the operational amplifier 55 and its inverting input.

The output of the operational amplifier 55 is coupled through a coupling resistor 61 to the non-inverting input of a digital comparator 63. The inverting input of the comparator 63 receives a preset reference voltage level which is determined by the tap terminal of a variable resistor 65. One end of the variable resistor 65 is coupled to ground, and its other end is coupled to a source of constant potential $V_r$ through a resistor 67. A reference diode 69 is coupled between ground and the end of the variable resistor 65. A feedback resistor 71 is connected between the output of the comparator 63 and its non-inverting input, and a current source including a resistor 73 and a fixed supply voltage $V_d$ is connected to the output of the comparator 63.

In the absense of output signals from buffering rectifiers 19 and 21, the diode 59 clamps the output of the operational amplifier 55 to a predetermined level in response to the current provided through the resistor 53. When output signals are present from the buffering rectifiers 19 and 21, the currents provided by such outputs are rapidly integrated by the operational amplifier 55 to provide an integrated output level which is proportional to the energy of the impact sensed by the microphone 11, 13 and the buffering rectifiers 19 and 21. After the impact ceases, the current provided through the resistor 53 is integrated back to the level determined by the clamping diode 59. Thus, the time duration that the output of the operational amplifier 55 is away from the clamp level determined by the diode 59 is proportional to the energy of the impact transmitted to the punching bag 15 and sensed by the microphones 11, 13.

The digital comparator 63 compares the output of the operational amplifier 55 with a reference level determined by the variable resistor 55 and its related circuitry. As long as the output of the operational amplifier 55 exceeds the predetermined reference level, the digital comparator 63 will provide a logic level pulse having a width which is proportional to the energy transmitted to the punching bag 15.

Figure 3:
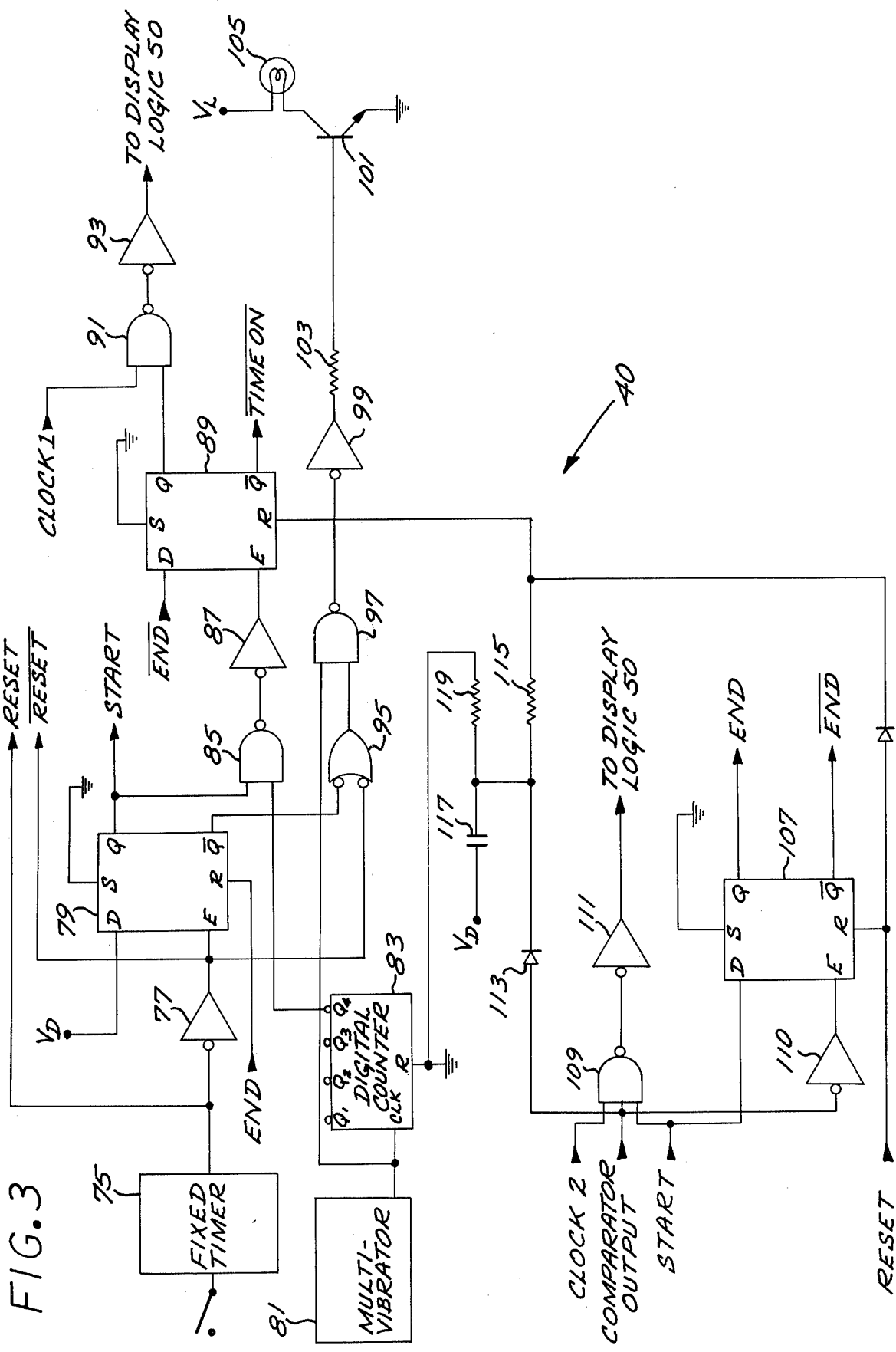
FIG. 3 is a circuit diagram of the timing circuit of the disclosed system.

The timing circuit generally indicated by the reference numeral 40 (FIG. 1) utilizes the comparator output provided by the digital comparator 63 and is disclosed in detailed form in FIG. 3. Specifically, the timing circuit 40 includes a fixed timer 75 which is actuated upon closure of the switch SW. The fixed timer 75 provides as an output a logic pulse of predetermined width which is utilized to reset particular logic circuitry in the timing circuit as indicated by the RESET designation on the line connected to the output of the fixed timer 75. An inverter 77 provides the inverse of the RESET signal to the C input of an RS flip-flop 79. The output of the inverter 77 is also utilized to provide a $\overline{\text{RESET}}$ to appropriate sections in the timing circuit as indicated by the $\overline{\text{RESET}}$ designation on the line connected to the output of the inverter 77. The RS flip-flop 79 toggles on the negative-going termination of the RESET signal pulse and provides a START/RUN signal at its Q output upon such toggling.

The actual start of the reaction time measuring function is controlled by the presence of the START/RUN signal and the output of a pseudo-random generator which includes an astable multivibrator 81 and a four-bit digital counter 83. The astable multivibrator 81 provides the clocking pulses to the digital counter 83 which has one of its outputs $Q_4$ connected to a dual input NAND-gate 85, which has its other input connected to the Q output (START/RUN) of RS flip-flop 79. The output of the NAND-gate 85 is connected to an inverter 87 which in turn is connected to the C input of an RS flip-flop 89. The flip-flop 89 has its reset terminal coupled to the RESET signal provided by the fixed timer 75 via a diode 91 and therefore provides a low level signal at its Q output during the presence of a RESET signal from the fixed timer 75. Thus, the RS flip-flop 89 will toggle when high level signals appear at both inputs of the NAND-gate 85, which will occur as a function of the state of the output of the digital counter 83 at the time the START/RUN signal from the Q output of the flip-flop 79 attains a high signal level. Of course, a high level signal must be present at the D input of the flip-flop 89 in order for its Q output to provide a high level output. An $\overline{END}$ signal is applied to the D input of the flip-flop 89. As discussed below, the $\overline{END}$ signal is at a high signal level when the START/CAP signal becomes high.

The other input of the NAND-gate 91 receives input clock pulses, designated as Clock 1 and has its output connected to an inverter 93. Thus, the inverter 93 provides clock pulses corresponding to Clock 1 at its output when the output Q of the RS flip-flop 89 is at a high level. Of course, during such time that the output Q has a high level output, the output $\overline{Q}$ is low. The output of the inverter 93 is applied to the display logic 50 (FIG. 1) to cause the display of the time during which the START/RUN signal from the flip-flop 79 remains in a high signal level, thereby indicating reaction time.

Further circuitry is provided to indicate that the timing circuit has been turned on but does not indicate that any measurements are being made. Specifically, such circuitry includes a negated-input OR-gate which has one input connected to the output of the inverter 77, and has its other input connected to the $\overline{Q}$ output of the RS flip-flop 79. The output of the negated-input OR-gate 95 is applied as an input to a NAND-gate 97 which has its other input coupled to the output of the astable multivibrator 81. The output of the NAND-gate 97 is connected to an inverter 99 which has its output coupled to the base of the transistor 101 through a coupling resistor 103. A light 105 is connected between a source of constant potential $V_L$ and the collector of the transistor 101, which has its emitter grounded. Thus, the light 105 will flash on and off at a rate determined by the astable multivibrator 91 during those times when the fixed timer 75 is providing a reset pulse, thereby providing a low input to the negated-input OR-gate 95, or when the $\overline{Q}$ output of the RS flip-flop 79 is providing a low signal to the negated-input OR-gate 95. When an END signal is applied to the reset terminal of the RS flip-flop 79, which END signal is discussed further below, the inputs to the negated-input OR-gate 95 will both be at a high level since the output of the fixed timer 75 will be at a low level. Therefore, such condition on the negated-input OR-gate will prevent the light 105 from flashing.

Referring now to the lower left hand portion of the circuit of FIG. 3, an RS flip-flop 107 is provided to control the end of the reaction time measuring period. The RS flip-flop 107 accepts at its D input the START/RUN signal provided by the RS flip-flop 79 which will allow the RS flip-flop to toggle when the input to its C input terminal changes from a high state to a low state. This transition is provided by an inverter 109 which accepts as its input the comparator output from the digital comparator 63 (FIG. 2) which will cause the RS flip-flop 107 to toggle when the comparator output indicates than an impact has been sensed. The RS flopflop 107 will provide an END signal at its Q output and an $\overline{END}$ at its $\overline{Q}$ output. The $\overline{END}$ output is provided as an input to the RS flip-flop 89 which will provide a low signal at its Q output when a low level signal is applied to its D input and a resetting pulse is applied to its R input which, as discussed below is provided by the output of the comparator 63 and an integrating circuit.

Thus, the RS flip-flop 89 will provide a low level signal to the NAND-gate 91 upon the occurrence of an impact, thereby preventing the transmission of Clock 1 pulses to the display logic 50. Such termination of the clock pulses indicates the end of the measured reaction time period.

The output from the digital comparator 63 (FIG. 2) is further utilized to provide to the display logic 50 information which is indicative of the energy of the impact. As discussed previously, the comparator output of the comparator 63 is a pulse having a width proportional to the energy of the impact transmitted to the punching bag 15. Such output from the comparator 63 and the START/RUN signal provided by the RS flip-flop 79 are utilized to enable a NAND-gate 109 and an inverter 111 to transmit clock pulses to the display logic 50. The clock pulses are provided as an input to the NAND-gate 109 as indicated by the designation Clock 2. As is readily evident, such clock pulses will be transmitted through the NAND-gate 109 and the inverter 111 only for the duration of an output pulse from the comparator 163, thereby indicating the energy of the impact by the number of clock pulses that are transmitted.

The comparator output pulse received from the comparator 63 is also utilized to reset the RS flip-flop 89 via the diode 113 and a resister 115. An integrating network including the source of constant supply $V_d$, a capacitor 117, and a resister 119, insures that a reset pulse of sufficient duration will be applied to the reset terminal of the RS flip-flop 89 upon the occurrence of an output from the comparator 63, thereby insuring sufficient time to allow the $\overline{END}$ signal applied to the D input of the RS flip-flop 89 to change from a high state to a low state when impact is sensed and signalled by the output of the comparator 63.

Figure 4:
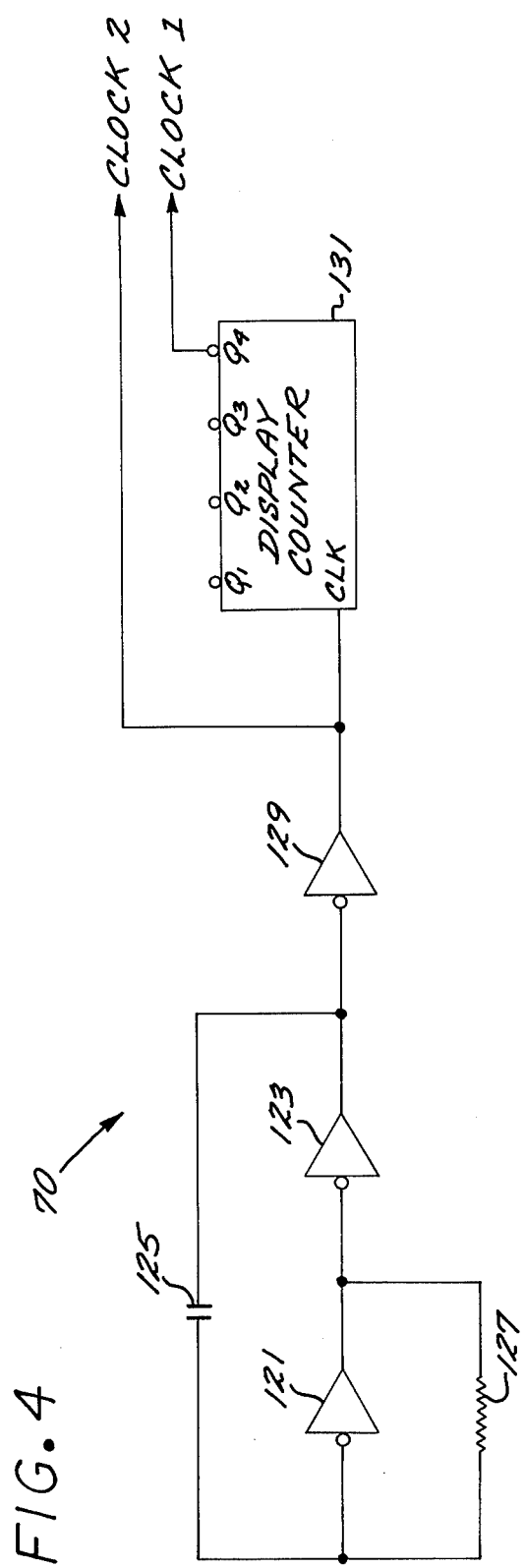
FIG. 4 is a circuit diagram of the circuitry for providing clocking signals for the timing circuitry for FIG. 3.

FIG. 4 illustrates a clock circuit 70 which can be used to provide the Clock 1 and Clock 2 pulses utilized by the NAND-gate 91 and the NAND-gate 109 in the timing circuit of FIG. 3. The clock circuit 70 includes inverters 121 and 123 which are serially arranged in an RC oscillator configuration with a feedback capacitor 125 connected between the output of the inverter 123 and the input of the inverter 121. A feedback resister 127 is connected across the inverter 121. An inverter 129 buffers the output of the RC oscillator provided by the inverter 123 and provides the Clock 2 pulses which are applied to the NAND-gate 109 (FIG. 3).

The output of the inverter 129 is also applied to the clock input of a decimal 4-bit counter 131. The output of the most significant bit $Q_4$ of the counter 131 is utilized for providing Clock 1 pulses to the NAND-gate 91 (FIG. 3).

Although the foregoing has been a disclosure of a particular embodiment of the claimed invention, it is apparent to one skilled in the art that modifications could be made to the disclosed system within the scope and spirit of the claims below which define the subject invention. For example, one skilled in the art could readily configure a display logic, with minor changes to the timing circuit, which would be responsive to multiple impacts, and which could control the display of the energy transmitted by each of the multiple impacts.

What is claimed is:

1. An athletic timing and energy measuring system for use by a participant, comprising:
   transducer means responsive to motional energy imparted by the participant for providing an output indicative of said motional energy;

logic means responsive to the output of said transducer means for providing a logical output pulse which is indicative of the start of the imparted motional energy, said logical output pulse further having a width proportional to said motional energy;

timing means responsive to external actuation for providing a start signal indicative of the start of a reaction time measurement period, said start signal being caused to occur after a pseudo-random delay after the external actuation, said timing means being further responsive to said logical output pulse for providing a first output representative of the participant's reaction time in response to said start signal and a second output representative of the amount of motional energy imparted by the participant in response to said start signal; and display means responsive to said timing means first and second outputs for visually displaying the participant's reaction time and the amount of motional energy imparted by the participant.

2. The measuring system of claim 1 wherein said transducer means comprises a pair of microphones spaced apart and attached to athletic apparatus for sensing motional energy imparted to the athletic apparatus by the participant.

3. The measuring system of claim 1 wherein said logic means includes means for rectifying said output of said transducer means, and means for integrating the rectified output from said rectifying means, thereby providing an integrated output.

4. The measuring system of claim 3 wherein said logic means further includes comparator means for comparing said integrated output with a reference level for providing said logical output pulse during such time when said integrated output exceeds the reference level.

5. The measuring system of claim 1 wherein said timing means includes:
    first gating means responsive to said start signal and said logic means logical output pulse for transmitting first clock pulses during the time between the occurrence of said start signal and the occurrence of said logical output; and
    second gating means responsive to said logical output pulse for transmitting second clock pulses for the duration of said logical output pulse.

6. The measuring system of claim 5 wherein said display means is responsive to said first and second clocks.

7. An athletic parameter measuring system for use by a participant, comprising:
    transducer means adapted to be responsive to predetermined athletic motion by the participant for providing an output indicative of the occurrence and presence of said predetermined motion;
    logic means responsive to said transducer output for providing an output pulse indicative of when said predetermined motion attains a predetermined status, and logic means output pulse having a width proportional to the motional energy of said predetermined motion; and
    timing means responsive to external actuation for providing a start signal, said start signal being caused to occur after a pseudo-random delay after the external actuation, said timing means being further responsive to said logic means output pulse for providing a first output during the time between the respective occurrences of said start signal and the initiation of said logic means output pulse and a second output during the presence of said logic means output pulse.

8. The measuring system of claim 7 wherein said timing means first output comprises a series of first clock pulses, the total count of said first clock pulses representing the time between the initiation of said start signal and the initiation of said logic means output pulse; and wherein said timing means second output comprises a series of second clock pulses, the total count of said second clock pulses representing the time duration of the presence of said logic means output pulse.

9. An athletic energy measuring system for use by a participant, comprising:
    transducer means responsive to motional energy imparted by the participant to an athletic apparatus, said transducer means providing an output indicative of said motional energy;
    logic means responsive to said transducer means output for providing a logical output pulse having a width proportional to said motional energy;
    timing means responsive to said logical output pulse for providing a timing output during the presence of said logical output pulse; and
    display means responsive to said timing means output for visually displaying the amount of said motional energy imparted by the participant.

10. The measuring system of claim 9 wherein said logic means includes:
    means for integrating information based on said transducer output for providing an integration output; and
    means for comparing said integration output with a reference signal level for providing said logical output pulse when said integration output exceeds the reference signal level.

11. The measuring system of claim 10 wherein said timing means includes clocking means for transmitting clock pulses to said display means during the presence of said logical output pulse from said logic means.

* * * * *